United States Patent
Ochsner et al.

[11] 3,959,396
[45] May 25, 1976

[54] UNSATURATED ALCOHOLS AND PERFUME COMPOSITIONS CONTAINING SAME

[75] Inventors: Paul Ochsner, Geneva; Bruno Peter Vaterlaus, Binningen, both of Switzerland

[73] Assignee: Givaudan Corporation, Clifton, N.J.

[22] Filed: Sept. 19, 1973

[21] Appl. No.: 398,887

Related U.S. Application Data

[63] Continuation of Ser. No. 657,501, Aug. 1, 1967, abandoned.

[30] Foreign Application Priority Data

Aug. 3, 1966 Switzerland............... 11292/66

[52] U.S. Cl................ 260/632 R; 252/522; 260/476 R; 260/488 H; 260/602; 260/615 A; 260/617 R; 260/618 R; 260/635 R; 260/635 M; 260/635 Y; 260/642 C
[51] Int. Cl.²............... C07C 33/02; C11B 9/00
[58] Field of Search............... 260/632 R, 631.5

[56] References Cited
UNITED STATES PATENTS

| | | | |
|---|---|---|---|
| 2,837,569 | 6/1958 | Verley | 260/631.5 |
| 3,217,041 | 11/1965 | Houlihan | 260/631.5 |
| 3,394,169 | 7/1968 | Davis | 260/632 R |

OTHER PUBLICATIONS

Jellinek, "The Practice of Modern Perfumery," (1954), translated by Krajkeman, pp. 145, 147.
West et al., "Synthetic Perfumes," (1949), pp. 24, 25.

*Primary Examiner*—Joseph E. Evans
*Attorney, Agent, or Firm*—Thomas Cifelli, Jr.

[57] ABSTRACT

A novel family of compounds, having desirable odorous qualities suitable for use in perfume compositions, is disclosed.

These compounds fall within the general formula:

a. a compound of the general formula:

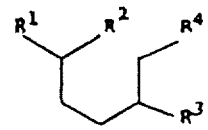

wherein
$R^1$ represents an alkyl group containing 1 to 4 carbon atoms,
$R^2$ is a member selected from the group consisting of an alkyl group containing 1 to 5 carbon atoms and a phenyl group,
$R^3$ is a member selected from the group consisting of H, a methyl group and an ethyl group, and
$R^4$ is a member selected from the group consisting of a CH$_2$OH group, a CH$_2$OAc group, wherein Ac denotes the acyl residue of a carboxylic acid, a CHO group, and an acetalised CHO group;

b. a compound as set forth in (a) above except that $R^1$ and $R^2$ together represent a member selected from the group consisting of a tetramethylene chain and a pentamethylene chain; and c. a compound selected from the group consisting of a $\Delta^5$-dehydro derivative of a compound as set forth in (a) and (b) above, a $\Delta^6$-dehydro derivative of a compound as set forth in (a) and (b) above, and a 6-hydroxy derivative of a compound as set forth in (a) and (b) above.

Numerous specific compounds, as well as processes for their preparation and perfume compositions utilizing the compounds, are disclosed.

6 Claims, No Drawings

UNSATURATED ALCOHOLS AND PERFUME COMPOSITIONS CONTAINING SAME

This is a continuation of applicant' application, Ser. No. 657,501, filed Aug. 1, 1967, now abandoned.

BACKGROUND OF THE INVENTION

This invention pertains to novel chemical compounds as set forth herinafter and to perfume compositions containing said compounds.

Although a number of classes of odorous chemical compounds is known, it has been found that the novel compounds of this invention possess outstanding and unexpected odorous properties.

SUMMARY OF THE INVENTION

This invention is concerned with perfume compositions which are characterised in that they contain a novel compound of the general formula

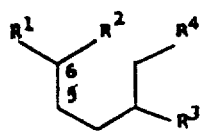

wherein
$R^1$ represents an alkyl group containing 1–4C,
$R^2$ represents an alkyl group containing 1–5C or a phenyl group,
$R^1$ and $R^2$ together represent a tetra- or pentamethylene chain,
$R^3$ represents a hydrogen atom, a methyl or ethyl group and
$R^4$ represents a $CH_2OH$ group or a $CH_2OAc$ group (wherein Ac denotes the acyl residue of a carboxylic acid) or an optionaily acetalised CHO group, or a $\Delta^{5-}$ or $\Delta^{6-}$ dehydro derivative or a g-hydroxy derivative or a compound of formula I.

DESCRIPTION OF THE PREFERRED EMBODIMENTS

Referring to the general formula given above, the preferred embodiments are as follows:

Examples of groups $R^1$ and $R^2$ are identical or different, straight-chain or branched alkyl groups such as methyl, ethyl, n-propyl, isopropyl, n-butyl, isobutyl. The Ac-group is preferably derived from lower aliphatic or aromatic carboxylic acids. Examples of such alkanoyl or aroyl groups are: formyl, acetyl, propionyl, butyryl, isobutyryl, benzoyl, cinnamyl. An optionally acetalised CHO group can, for example, be present as a di(lower alkyl) acetal or as a lower alkylene acetal.

The said $\Delta^{5-}$ and $\Delta^{6-}$ dehydro derivatives can be represented by general formula II:

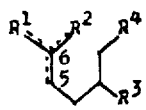

The broken lines starting from the $C_6$ atom represent a carbon double bond which can be located in one of the three positions. Formula II accordingly encompasses the formulae IIa, IIb and IIc (inclusive of the racemic and optically active forms, as well as cis-trans isomers) which are set out hereafter:

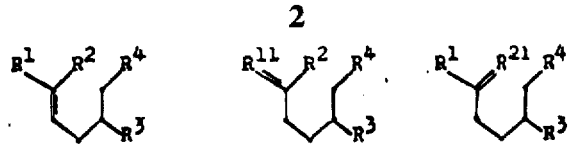

In these formulae, the symbols $R^1$–$R^4$ have the same significance as given above. $R^{11}$ and $R^{21}$ represent alkylidene groups corresponding to the alkyl groups $R^1$ and $R^2$, respectively, such as, $=CH_2$ or $=CH—CH_3$.

The compounds of the general formula I possess special odoriferous properties. Therefore, they may be used in perfume compositions, e.g. for imparting odors to alcoholic solutions, scaps, solid and liquid detergents, aerosols, cosmetics of any kind, such as creams, face cleansing milk, fards, lipsticks, bathing salts and oils. In these perfumed products the content of the scented compounds can vary between 1‰ (detergents) and about 20% (alcoholic solutions). Concentrates having e.g. the folloing composition may be used for perfuming:

| Compound of the general formula I | 2–90% |
|---|---|
| fixative (e.g. macrocyclic muso) | 1– 2% |
| additives of floral note (e.g. linalyl acetate, ylang-ylang | 5–10% |
| additives of fresh note (e.g. linalool) | 3– 5% |
| additives imparting the basic note (e.g. cinnamyl alcohol, sandela) | 5–10% |

The compounds of formula II possess outstanding odoriferous properties. The corresponding alcohols (i.e. compounds of formula II wherein $R^4$ represents $CH_2OH$) generally possess a rose-, lilac- or lily of the valley-like odour. The compounds of formulae IId and IIe display special odour properties:

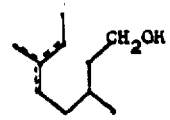 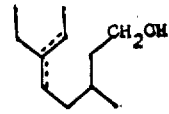

Formula IId encompasses 3,6-dimethylocten-(5)-ol-(1), the corresponding octene-(6) isomer [i.e. 3,6-dimethylocten-(6)-ol-(1)] and 6-ethyl-3-methylhepten-(6)-ol-(1). Formula IIe encompasses 6-ethyl-3-methyl-octen-(5)-ol-(1) and its octene-(6) isomer, i.e. 6-ethyl-3-methyl-octen-(6)-ol-(1).

The Table I shows the odour notes of unsaturated alcohols of formula II, $R^3$ in all cases signifying a $CH_3$ group and $R^4$ in all cases signifying a $CH_2OH$ group:

Table I

| $R^1$ | $R^2$ | Odour-characteristic |
|---|---|---|
| $CH_3$ | $CH_3$ | Green, floral odour; with a nuance reminiscent of lilac leaves. |
| $CH_3$ | $C_2H_5$ | Lily of the valley slightly rose-like. |
| $CH_3$ | $n-C_3H_7$ | Green, floral. |
| $CH_3$ | $iso-C_3H_7$ | Fresh, rose-like. |
| $CH_3$ | $iso-C_4H_9$ | Floral, rose-like. |
| $CH_3$ | $sec-C_4H_9$ | Fresh, mint-like note. |
| $CH_3$ | $tert-C_4H_9$ | Delicately rose-like. |
| $CH_3$ | $n-C_5H_{11}$ | Fruit like, reminiscent of pineapple. |
| $C_2H_5$ | $n-C_3H_7$ | Roses. |
| $C_2H_5$ | $n-C_4H_9$ | Delicately rose-like. |

Table I-continued

| R¹ | R² | Odour-characteristic |
|---|---|---|
| n-C₃H₇ | n-C₃H₇ | Roses, lily of the valley. |
| iso-C₃H₇ | iso-C₃H₇ | floral, lilac-note. |
| iso-C₄H₉ | iso-C₄H₉ | delicately woody, spicy. |
|  | —(CH₂)₄— | rose-like, soft. |
|  | —(CH₂)₅— | styrax odour, animal. |
| C₂H₅ | C₂H₅ | lily of the valley, roses. |

The said 6-hydroxy derivatives can be represented by general formula III:

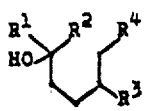

III wherein
R¹-R⁴ have the above significance.
Especially interesting 6-hydroxy-derivatives are the diols of the general formula

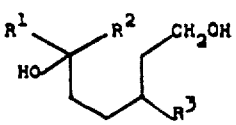

VII wherein
R¹-R³ have the same significance as above.
These diols exert a stabilizing and fixative effect. They may be added to the odorants e.g. alcohols or aldehydes, to be fixed in amounts of, e.g., 1–50% by weight. Examples of alcohols and aldehydes that may be stabilized or fixed by the diols of formula VII, such as 3,6-dimethyl-octanediol-(1.6) or 6-ethyl-3-methyl-octanediol-(1,6), are: citronellol, unsaturated alcohols of the general formula

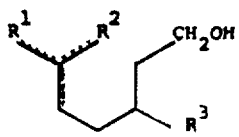

VIII wherein
R¹-R³ have the same significance as above, cyclamen aldehyde, Lilial, Buxine, n-decanal, 2-methyl-undecanal, etc. An especially marked fixative action is exerted by the diols of formula VI upon those alcohols which can be obtained from the diols by dehydration. Thus, e.g. 6-ethyl-3-methyl-octanediol-(1,6) is an especially good fixative for the corresponding unsaturated alcohol IIe.

The percentages may vary depending upon the uses of the concentrates. Examples of concentrate that are suitable, e.g., for soaps and other cosmetic products, as well as for alcoholic solutions, are the following:

| Lily of the valley composition | Parts by weight |
|---|---|
| Alcohol of formula IId | 50 |
| Cinnamyl alcohol | 10 |
| Benzyl acetate | 10 |
| α-Amylcinnamaldehyde | 5 |
| Ylang-ylang essence | 5 |
| Linalool | 5 |
| Phenylethyl alcohol | 15 |
| Alcohol of formula IId or IIe | 655 |
| Lauryl aldehyde | 15 |

| Lily of the valley composition | Parts by weight |
|---|---|
| Hexenyl acetate (10% in D.P.G.*) | 10 |
| Benzyl acetate | 10 |
| Heliotropin | 10 |
| Amyl phenylacetate (10% in D.P.G.) | 10 |
| Sandal | 25 |
| Benzyl isobutyrate | 25 |
| Phenylethyl alcohol | 40 |
| α-Hexyl-cinnamaldehyde | 50 |
| Dimethyl benzyl carbinol | 50 |
| Cinnamyl alcohol | 100 |
|  | 1000 |

| Lilac composition | Parts by weight |
|---|---|
| Alcohol of formula IId or IIe | 500 |
| Ylang Bourbon | 30 |
| Benzyl acetate | 30 |
| α-Hexylcinnamaldehyde | 40 |
| Phenylacetaldehyde (10% in D.P.G.) | 50 |
| Cinnamyl alcohol | 100 |
| Heliotropin | 100 |
| Isoeugenol | 50 |
| Terpineol | 100 |
|  | 1000 |

*Dipropylene glycol

The following concentrate is especially suitable for alcoholic solutions:

|  | Parts by weight |
|---|---|
| Alcohol of formula IIe | 250 |
| vetivenyl acetate | 200 |
| jasmine, absolute | 100 |
| cinnamyl alcohol | 70 |
| turkish rose oil | 150 |
| ylang-ylang | 50 |
| oak moss | 40 |
| patchouli | 30 |
| n-decyl aldehyde (10% in D.P.G.) | 10 |
| undecyl aldehyde (10% in D.P.G.) | 20 |
| castor resin | 25 |
| pentadecanolid | 20 |
| isobutyl quinoline (1% in D.P.G.) | 20 |
| undecalactone (50% in D.P.G.) | 15 |

The fragrances of these concentrates may be modified e.g. by substituting for the unsaturated alcohols IId or IIe in the foregoing formulations, unsaturated esters of the general formula

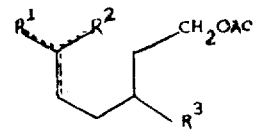

IX or corresponding unsaturated aldehydes of the general formula

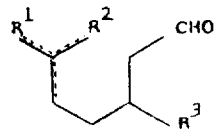

X or corresponding saturated alcohols of the general formula

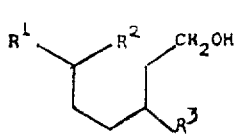

XI or corresponding unsaturated acetals of the general formula

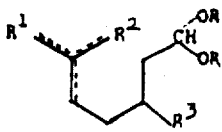

In these formulae, the symbols $R^1$–$R^3$ and Ac have the same meaning as above, and the symbols R of formula XV represent lower alkyl groups that also may be linked together.

A concentrate with an unsaturated aldehyde of formula X may, e.g., contain the following ingredients:

|  | Parts by weight |
|---|---|
| Aldehyde of formula X ($R^1$—$R^2$—ethyl, $R^3$—methyl) | 5 |
| benzyl acetate | 20 |
| cinnamyl alcohol | 20 |
| α-amyl cinnamaldehyde | 10 |
| ylang-ylang | 10 |
| linalool | 10 |
| phenyl ethyl alcohol | 25 |

The following is illustrative of compositions containing diols of the general formula VII:

| Lilac composition | Parts by weight |
|---|---|
| diol of the formula VII ($R^1$—$R^2$—ethyl, $R^3$—methyl) | 150 |
| alcohol of formula IIe | 350 |
| ylang bourbon | 30 |
| benzyl acetate | 30 |
| α-hexyl cinnamaldehyde | 40 |
| phenylacetaldehyde (10% in D.P.G.) | 50 |
| cinnamyl alcohol | 100 |
| heliotropin | 100 |
| isoeugenol | 50 |
| terpineol | 100 |

| perfume of rose type | Parts by weight |
|---|---|
| diol of formula VII ($R^1$—ethyl, $R^2$—$R^3$—methyl) | 200 |
| phenyl ethyl alcohol | 200 |
| geraniol | 370 |
| citronellol | 70 |
| linalool | 30 |
| phenyl ethyl acetate | 10 |
| phenylacetaldehyde (10% in D.P.G.) | 5 |
| dimethylbenzylcarbinol acetate | 10 |
| α-ionone | 5 |

| perfume of jasmine type | Parts by weight |
|---|---|
| diol of formula VII ($R^1$—ethyl, $R^2$—$R^3$—methyl) | 250 |
| benzyl acetate | 380 |
| α-amylcinnamaldehyde | 100 |
| phenyl ethyl alcohol | 150 |
| indol (20% in D.E.P.*) | 20 |
| methyl anthranilate | 10 |
| ylang bourbon | 60 |
| linalool | 20 |
| undecalactone (10% in D.P.G.) | 10 |

*Diethyl phthalate

The following reaction scheme presents a summary of the preparative possibilities for the manufacture of compounds of formulae I, II and III:

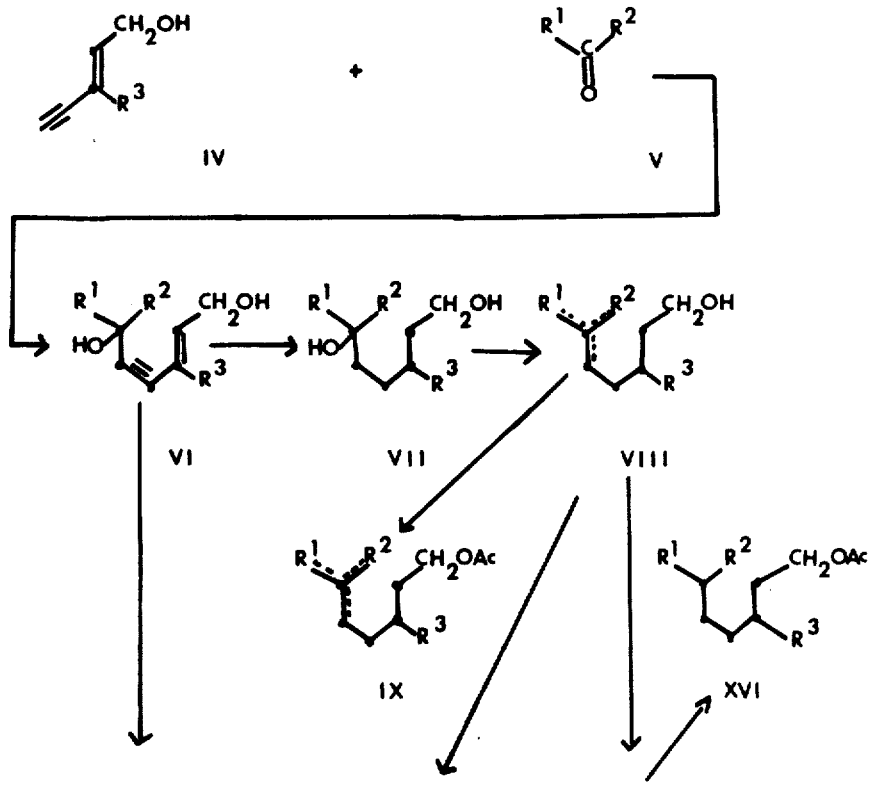

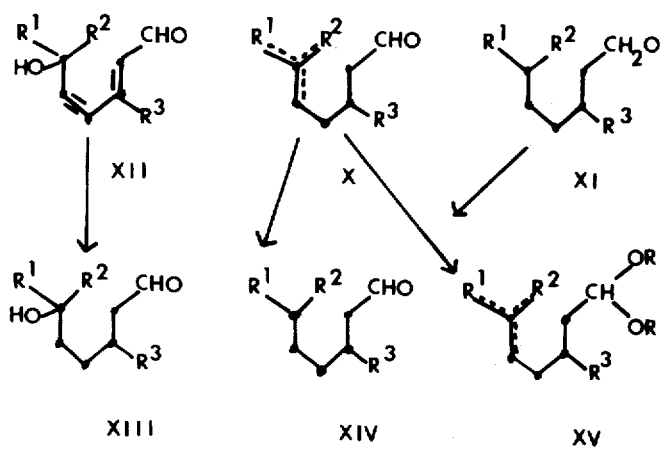

In these formulae,

R¹–R³, as well as Ac, have the above significance. The symbols R of formula XV signify lower alkyl groups which may be linked together.

By condensation of an acetylenically unsaturated alcohol of formula IV with a ketone of formula V there is obtained the diol of formula VI. The condensation can be undertaken according to the methods which are known for the ethynylation of ketones: for example, a. using a Grignard compound (e.g. by means of ethyl magnesium bromide or methyl magnesium chloride);

b. using potassium hydroxide [see A. W. Johnson: The Chemistry of Acetylenic Compounds, Vol.I (London 1946), pages 6–16];

c. in liquid ammonia [see R. A. Raphael: Acetylenic Compounds in Organic Synthesis (London 1955), pages 1–14; W. Ried; Neuere Methoden der praparativen organischen Chemie IV. Aethinierungsreaktionen I. Angew. Chemie, 1964, 76, 933–944].

By hydrogenation of the unsaturated diol compounds of formula VI, there can be obtained the corresponding saturated diols of formula VII; for example, by catalytic hydrogenation by means of Raney-nickel in the presence of a solvent such as methanol or ethanol. At the beginning of the hydrogenation, the temperature is conveniently held at approximately 20° and then increased somewhat (e.g. to about 60°–80°) towards the end of the hydrogenation. If necessary, the hydrogenation can also be taken to conclusion under pressure (e.g. under a pressure of about 20 atm.). Since the hydrogenation of the acetylene bond proceeds exothermically, it is recommended to cool the reaction mixture at the beginning of the hydrogenation.

The saturated diols VII can be converted into the olefinically unsaturated primary alcohols of formula VIII with dehydrating agents. The dehydration yields a mixture of isomeric compounds which differ from each other by the location of the newly introduced double bond (see the types of the formulae IIa, IIb and IIc). In the case of identity of R¹ and R², the number of isomers is of course reduced.

Sutable dehydration agents are, for example, acidic salts such as potassium bisulphate, with which yields of up to 90% of the theory may be achieved. However, other catalysts which are known to be useful for the dehydration of tertiary alcohols (such as iodine or phosphoric acid) can also be used.

The alcohols of formula VIII may be esterified in the usual manner, compounds of formula IX being obtained which are likewise distinguished by special perfume properties. The odour-notes of esters of formula IX are compiled in the following Table II ($R^3$: $CH_3$):

Table II

| $R^1$ | $R^2$ | Ac | Odour characteristic |
|---|---|---|---|
| $CH_3$ | $C_2H_5$ | formyl | floral, woody. |
| $CH_3$ | $C_2H_5$ | acetyl | floral, reminiscent of leaves. |
| $CH_3$ | $C_2H_5$ | butyryl | soft, floral. |
| $C_2H_5$ | $C_2H_5$ | formyl | floral. |
| $C_2H_5$ | $C_2H_5$ | acetyl | fresh, floral |
| $C_2H_5$ | $C_2H_5$ | butyryl | floral, with animal note |
| $C_2H_5$ | $C_2H_5$ | isobutyryl | floral. |
| n-$C_3H_7$ | n-$C_3H_7$ | acetyl | delicately floral, reminiscent of jasmine. |
| —$(CH_2)_5$— | | acetyl | fatty, delicately animal. |
| $CH_3$ | n-$C_3H_7$ | acetyl | fruit-like |
| $CH_3$ | tert-$C_4H_9$ | formyl | delicately fruit-like |
| $CH_3$ | iso-$C_4H_9$ | formyl | green, floral. |

By oxidation of the primary alcohol group to the aldehyde group according to known methods the aldehydes of formula X can be obtained from the corresponding alcohols of formula VIII. These aldehydes are also interesting perfumes. Thus, for example, the aldehyde of formula X wherein $R^1$ and $R^2$ are ethyl and $R^3$ is methyl possesses a pleasant green, floral odour.

The saturated aldehydes of formula XIV and the acetals of formula XV can be manufactured from the unsaturated aldehydes of formula X by known hydrogenation and acetalisation methods.

By addition of one mole of hydrogen at the double bond of the alcohols VIII by means of catalytic hydrogenation, the corresponding saturated alcohols of formula XI may be manufactured. Suiable hydrogenation catalysts, are for example, palladium or Raney-nickel. These saturated alcohols are also interesting perfumes. The odour-notes of a few representatives of the group XI are compiled in Table III. ($R^3$: $CH_3$):

Table III

| $R^1$ | $R^2$ | Odour characteristic |
|---|---|---|
| $CH_3$ | $C_2H_5$ | floral, green; reminiscent of lily of the valley. |
| $C_2H_5$ | $C_2H_5$ | floral, related to lily of the valley. |
| $CH_3$ | iso-$C_3H_7$ | rose-like. |

By oxidation of the primary alcohol group of the acetylenic diols VI (e.g. by means of manganese dioxide), there are obtained the corresponding acetylenic hydroxy-aldehydes XII which can be converted in a known manner (e.g. with palladium/carbon under normal conditions), into the saturated hydroxyaldehydes XIII. Examples of such aldehydes are: 6-hydroxy-3,6-dimethyl-octanal (leaf-odour with lilac-wood note), 6-hydroxy-6-ethyl-3-methyl-octanal (in comparison with hydroxydihydro-citronellal, greener and somewhat less soft in odour) and 6-hydroxy-3,6,7-trimethyl-octanal.

The invention is further illustrated by the following examples, without, however, limiting it to them. The temperatures given in this specification are in degrees Centigrade, unless otherwise stated. All boiling points are uncorrected.

In the following Examples, the temperatures are given in degrees centigrade.

A. Manufacture of compounds of formula VI:

EXAMPLE 1

In a 5 litre flask there are placed 600 g of powdered potassium hydroxide and 1200 g of dry methylal and thereupon, with stirring at −20° to −10°, 288 g of trans 3-methyl-penten-(2)-yn-(4)-ol-(1). 284 g of diethyl ketone are then added with stirring at −10°. The temperature is thereupon allowed to rise to +20°, the reaction mixture decomposed with 1200 ml of water and extracted with 1800 ml of toluene. The organic phase is washed neutral with 2000 ml of water. After evaporation of the solvent, there are obtained 529 g of crude product which after distillation yields 498 g of trans 6-ethyl-3-methyl-octen-(2)-yne-(4)-diol-(1,6). B.p. 125°–135°/0.015 mm; $n_D^{20} = 1.5088$.

EXAMPLE 2

In the manner described in the Example 1, from trans 3-methyl-penten-(2)-yn-(4)-ol-(1) and methyl ethyl ketone there is obtained trans 3,6-dimethyl-octen-(2)-yne-(4)-diol-(1,6). B.p. 125°–135°/0.04 mm; $d_4^{20} = 0.9871$, $n_D^{20} = 1.5090$. Yield 76%.

EXAMPLE 3

96 g of trans 3-methyl-penten-(2)-yne-(4)-ol-(1) in 200 ml of dry ether are added dropwise to a suspension of lithium amide manufactured from 14.5 g of lithium in 1500 ml of liquid ammonia. After stirring for 2 hours, 70 g of acetone in 200 ml of tetrahydrofuran are slowly added. The excess ammonia is allowed to evaporate and 1 liter of tetrahydrofuran is added. The reaction mixture is decomposed in the cold with 200 ml of water and the tetrahydrofuran evaporated off. The residue is taken up in ether. The ether solution is washed neutral and the solvent evaporated. After distillation, there are obtained 30 g of trans 3,6-dimethyl-hepten-(2)-yne-(4)-diol-(1,6). B.p. 158°/0.06 mm; $d_4^{20} = 1.0007$, $n_D^{20} = 1.5099$. Yield 20%.

EXAMPLE 4

Ethyl magnesium bromide is manufactured from 44 g of magnesium and 220 g of ethyl bromide in 400 ml of dry ether. 200 ml of toluene are added and the mixture is slowly treated, between 30° and 40°, with a solution of 79.2 g of cis-3-methyl-penten-(2)-yn-(4)-ol-(1) in 200 ml of dry toluene. The reaction mixture is held at 50° for 3 hours and then cooled to 10°. At this temperature there is added a solution of 50.4 g of methyl ethyl ketone in 200 ml of dry toluene. After 3 hours at 60°, the reaction mixture is cooled and decomposed with a saturated solution of 80 g of ammonium chloride in 500 ml of ice-water. The mixture is washed with a saturated tartaric acid solution and then with water up to the neutral reaction. After evaporation of the solvent, 86.5 g of crude product are obtained which, after purification by means of distillation, yield 78.0 g of cis-3,6-dimethyl-octen-(2)-yne-(4)-diol-(1,6). B.p. 135°–140°/0.04 mm; $n_D^{20} = 1.4908$; $d_4^{20} = 0.9845$. Yield 66.2%.

EXAMPLE 5

In a 2 liter flask, there are placed 200 g of powdered potassium hydroxide and 600 ml of dry methylal and thereupon, at −10° with stirring, 96.1 g of a mixture of cis and trans 3-methyl-penten-(2)-yn-(4)-ol-(1)[cis:trans = 83:17]. 95 g of diethyl ketone are then added at −10°, the temperature is allowed to rise to +20° and the mixture decomposed with 400 ml of water. The reaction mixture is then taken up in 600 ml of toluene and the organic phase washed neutral with 700 ml of water. After evaporation of the solvent, there are obtained 84 g of crude product which after distillation yields 58.8 g of a mixture of cis and trans 6-ethyl-3-methyl-octen-(2)-yne-(4)-diol-(1,6), the proportion of cis:trans being = 62:38. Yield 32.3%.

EXAMPLE 6

Ethyl magnesium bromide is prepared from 13.4 g of magnesium and 67.3 g of ethyl bromide in 60 ml of dry ether. 65 ml of dry toluene are added and the solution obtained is slowly poured at 30°–40°, into a solution of 27.5 g of a mixture of cis and trans 3-ethyl-penten-(2)-yn-(4)-ol-(1) in 60 ml of dry toluene. The reaction mixture is kept for 3 hours at 50° and cooled to 10°, whereupon a solution of 12.5 g of acetone in 60 ml of dry toluene is added thereto. The reaction mixture is kept for 3 hours at 60°, then cooled and decomposed by means of a saturated ammonium chloride solution. The organic fraction is washed with a tartaric acid solution, then with water until neutral. 23.2 g of 3-ethyl-6-methyl-hepten-(2)-yne-(4)-diol-(1,6) [mixture of cis- and trans-isomers] are thus obtained. B.p 110°–125°/0.1 mm; $n_D^{20} = 1.4971$. Yield 85%.

EXAMPLE 7

25.9 g of 3-ethyl-6-methyl-octen-(2)-yne-(4)-diol-(1,6) are obtained in an analogous manner from 24.8 g of 3-ethylpenten-(2)-yn-(4)-ol-(1) [mixture of cis- and trans-isomers] and 14.0 g of methyl ethyl ketone. B.p. 100°–125°/0.01 mm; $n_D^{20} = 1.4995$. Yield 74%.

EXAMPLE 8

32.5 g of 3,6-diethyl-octen-(2)-yne-(4)-diol-(1,6) [mixture of cis- and trans-isomers] are obtained in an analogous manner from 27.5 g 3-ethyl-penten-(2)-yn-(4)-ol-(1) [mixture of cis- and trans-isomers] and 18.5 g of diethyl ketone. B.p. 115°–125°/0.03 mm; $n_D^{20} = 1.5008$. Yield 77%.

EXAMPLE 9

According to the method described in Example 1 penten-(2)-yn-(4)-ol-(1) is reacted with methyl ethyl ketone to form trans 6-methyl-octen-(2)-yne-(4)-diol-(1,6). B.p. 102°/0.03 mm; $d_4^{20} = 1.005$; $n_D^{20} = 1.5135$. Yield 45%.

B. Manufacture of compounds of formula VII:

EXAMPLE 10

88.2 g of trans 3,6-dimethyl-octen-(2)-yne-(4)-diol-(1,6) are dissolved in 200 ml of methanol and hydrogenated at 20° under atmospheric pressure in the presence of 10 g of Raney-nickel. The amount of hydrogen to be theoretically taken up amounts to 38715 ml. After 8 hours, 30,000 ml of hydrogen have been taken up. A further 5 g of catalyst are then added and the hydrogenation continued at 60°. The absorption slows down after 8 hours. A further 10 g of catalyst are therefore added and the mixture is further hydrogenated at 60°. After the uptake of the theoretical amount of hydrogen, the $H_2$-absorption practically ceases. The catalyst is filtered off and the solvent evaporated. After distillation, there are obtained 81.3 g of 3,6-dimethyl-octanediol-(1,6). B.p. 92°–95°/0.01 mm; $d_4^{20} = 0.9413$; $n_D^{20} = 1.4625$. Yield 89%.

EXAMPLE 11

In the manner described in Example 10, using ethanol as the solvent, from 467.4 g of trans 6-ethyl-3-methyl-octen-(2)-yne-(4)-diol-(1,6) there are obtained 440 g of 6-ethyl-3-methyl-octanediol-(1,6). B.p. 108°–115°/0.05 mm; $d_4^{20} = 0.9425$; $n_D^{20} = 1.4665$; yield 91.5%.

EXAMPLE 12

22.9 g of 3-ethyl-6-methyl-hepten-(2)-yne-(4)-diol-(1,6) [mixture of cis- and trans-isomers] are hydrogenated at 20° with 5 g of Raney-Nickel in 100 ml of ethanol until the uptake of hydrogen slows down after 9 hours, i.e. up to the absorption of about 7000 ml of hydrogen (theoretical amount: 10400 ml). After the addition of a further 5 g of Raney-Nickel, the hydrogenation is continued at 60°. When the uptake again slows down (towards 9000 ml), the hydrogenation is pursued at a pressure of 20 atm. and a temperature of 80° until the absorption ceases. The catalyst is then filtered off, the alcohol evaporated and the residue (27 g) distilled in high vacuo. There are thus obtained 15.8 g of d,1-3-ethyl-6-methyl-heptanediol-(1,6) of b.p. 98°/0.06 mm; $n_D^{20} = 1.4618$. Yield 67%.

EXAMPLE 13

By the hydrogenation of 3-ethyl-6-methyl-octen-(2)-yne-(4)-diol-(1,6) [mixture of cis- and trans-isomers] according to the method described in Example 12, there is obtained the d,1-3-ethyl-6-methyl-octanediol-(1,6) of b.p. 108°/0,05 mm; $n_D^{20} = 1.4655$. Yield 57%.

EXAMPLE 14

By the hydrogenation of 3,6-diethyl-octen-(2)-yne-(4)-diol-(1,6) [mixture of cis- and trans-isomers] according to the method described in Example 12, there is obtained the d,1-3,6-diethyl-octanediol-(1,6) of b.p. 90°/0.03 mm; $n_D^{20} = 1.4697$. Yield 77%.

EXAMPLE 15

By the hydrogenation of trans 6-methyl-octen-(2)-yne-(4)-diol-(1,6) according to the method described in Example 12, there is obtained the d, 1-6-methyl-octanediol-(1,6)- of b.p. 103°/0.1 mm; $d_D^{20} = 0.9469$; $n_D^{20} = 1.4625$. Yield 76%:

C. Manufacture of compounds of formula VIII:

EXAMPLE 16 a. 437 g of 6-ethyl-3-methyl-octanediol-(1,6) are slowly added to a Claisen flask containing 20 g of potassium bisulphate and heated to 150°–160°. After reduction of the pressure to 12 mm, the unsaturated alcohol which is formed is distilled at 120°–123°. It is taken up in 1000 ml of toluene, washed with 100 ml of aqueous sodium carbonate and then with water until neutral. The toluene is evaporated and the crude product (415 g) obtained fractionally distilled. There are thus obtained 338.4 g of a mixture of 6-ethyl-3-methyl-octen-(5)-ol-(1) and the corresponding octene-(6) isomer. B.p. 90°–95°/3 mm; $d_4^{20} = 0.8623$; $n_D^{20} = 1.4610$. Yield 86%.

b. Part (a) of this example was repeated, using 407 grams of 3,6-dimethyl-octanediol-(1,6) in place of the diol used in part (a). There was thus obtained 309 g. of a mixture of 3,6-dimethyl-octen-(5)-ol-(1), the corresponding octene-(6)-isomer and 6-ethyl-3-methyl-hepten-(6)-ol-(1). B.P. 83°–125°/3 mm, with the main quantity distilling at 87°; $d_4^{20} = 0.8590$; $n_D^{20} = 1.4545$ to 1.4573.

EXAMPLE 17

7.8 g of 3,6,7-trimethyl-octanediol-(1,6) are distilled between 100° and 120° at 11 mm in the presence of 0.5 g of iodine. 0.5 g of water are thus removed. The mixture is taken up in ether, washed with a solution of sodium sulphite and then with water. After drying and evaporation of the solvent, there are obtained 5.3 g of a mixture containing 3,6,7-trimethyl-octen-(5)-ol-(1), 6-isopropyl-3-methyl-hepten-(6)-ol-(1) and 3,6,7-trimethyl-octen-(6)-ol-(1). The mixture of the pure products is obtained by distillation. B.p. 90°–95°/3mm; $n_D^{20} = 1.4620$; yield 75.6%.

EXAMPLE 18

11.6 g of 3-methyl-6-propyl-nonanediol-(1,6) are slowly added to 40% phosphoric acid which is heated to boiling. The dehydrated alcohol is removed as it is formed with the steam. The dehydration is practically completed after 4 hours. The distillate is taken up in ether and the ether solution washed neutral. After evaporation of the solvent, there are obtained 7.3 g of a crude mixture of 3-methyl-6-propyl-nonen-(5)-ol-(1) and the corresponding nonene-(6)-isomer. The pure mixture boils at 111°/3 mm; $d_4^{20} = 0.8555$; $n_D^{20} = 1.4600$.

EXAMPLE 19

10.3 g of d,1-3-ethyl-6-methyl-heptanediol-(1,6) are heated to 135°–155° in the presence of 0.5 g of potassium bisulfate. The dehydrated product is distilled under diminished pressure (25 mm). The distillation product is taken up in ether and washed with water. After drying and evaporating off the solvent, there are obtained 9.3 g of a crude product, the distillation of which gives 6.3 g of a mixture of 3-ethyl-6-methyl-hepten-(5)-ol-(1) and of the corresponding heptene-(6)-isomer. B.p. 88°/4 mm; $d_4^{20} = 0.8603$; $n_D^{20} = 1.4575$. Yield 69%. Odour of lily of the valley, lilac and roses.

EXAMPLE 20

By dehydrating 11 g of d,1-3-ethyl-6-methyl-octanediol-(1,6) according to the method described in Example 19, there are obtained 5.7 g of a mixture of d,1-3-ethyl-6-methyl-octen-(5)-ol-(1), of the corresponding octene-6)-isomer and of d,1-3,6-diethyl-hepten-(6)-ol-(1). B.p. 98°/4 mm; $d_4^{20} = 0.8639$; $n_D^{20} = 1.4600$. Yield 57%. Floral odour of lily of the valley and roses.

EXAMPLE 21

By dehydrating 10.7 g of d,1-3,6-diethyl-octanediol-(1,6) according to the method described in Example 19, there are obtained 7.9 g of a mixture of d,1-3,6-diethyl-octen-(5)-ol-(1) and of the corresponding octene-(6)-isomer. B.p. 108°/4 mm; $d_4^{20} = 0.8649$; $n_D^{20} = 1.4625$. Yield 81%. Odour of lily of the valley and linden, strongly adhesive.

EXAMPLE 22

By dehydrating d,1-6-methyl-octanediol-(1,6) according to the method described in Example 19, there are obtained a mixture of 6-methyl-octen-(5)-ol-(1), of the corresponding octene-(6)-isomer and of 6-ethyl-hepten-(6)-ol-(1). B.p. 95°–100°/3 mm; $d_4^{20} = 0.8604$; $n_D^{20} = 1.4542$. Yield 60%. Odour of water-melon and cucumber.

D. Manufacture of compounds of formula IX:

EXAMPLE 23

23 g of 98% formic acid are added in the course of 20 minutes at 45° to 46 g of acetic anhydride. After 2 hours, 45.3 g of a mixture of 3,6-dimethyl-octen-(5)-ol-(1), the corresponding octene-(6)-isomer and of 6-ethyl-3-methyl-hepten-(6)-ol-(1) are added at 5°–10°. The temperature is held below 10° for 4 hours. After allowing to stand at room temperature for 3 days, the reaction product is poured on 250 g of ice, extracted with ether and washed neutral. After evaporation of the solvent, there are obtained 51.9 g of crude product from which 42.2 g of a mixture of the formates of the alcohols named above in this example may be isolated by distillation. B.p. 76°/3 mm; $d_4^{20} = 0.9032$; $n_D^{20} = 1.4452$; yield 79%.

EXAMPLE 24

A solution of 0.38 g of o-phosphoric acid in 27.5 g of acetic anhydride is added to 42.5 g of a mixture of 6-ethyl-3-methyl-octen-(5)-ol(1) and the corresponding octene-(6) isomer. The mixture, which is cooled during the addition, is subsequently heated at 60° for 3 hours. After working up, there are obtained 52.6 g of crude product and therefrom, by distillation, 44.5 g of a mixture of the acetates of the alcohols named above in this example. B.p. 107°/5 mm; $d_4^{20} = 0.8913$; $n_D^{20} = 1.4470$. Yield 84%.

E: Manufacture of compounds of formula X:

EXAMPLE 25

A solution of 36 g of sodium bichromate, 37 g of water and 58 g of 60% sulphuric acid is slowly added with stirring and with external cooling to 20 g of water and 40 g of a mixture of 6-ethyl-3-methyl-octen-(5)-ol-(1) and the corresponding octene-(6)-isomer. In doing so, the temperature is held below 20°. The mixture is stirred for a further hour and then taken up in toluene and washed neutral. After evaporation of the solvent, there are obtained 30 g of crude product and, therefrom, a mixture of 6-ethyl-3-methyl-octen-(5)-al and the corresponding octene-(6) isomer. B.p. 71°/4 mm; $n_D^{20} = 1.4514$.

EXAMPLE 26

By oxidation, according to the method described in Example 25, of a mixture of d,1-3,6-dimethyl-octen-(5)-ol-(1), of the corresponding octene-(6)-isomer and of d,1-6-ethyl-3-methyl-hepten-(6)-ol-(1), there is obtained a mixture of d,1-3,6-dimethyl-octen-(5)-al-(1), of the corresponding octene-(6)-isomer and of d,1-6-ethyl-3-methylhepten-(6)-al-(1) of b.p. 68°/4 mm; $d_4^{20} = 0.8773$; $n_D^{20} = 1.4477$. Original green and floral odour.

F. Manufacture of compounds of formula XI:

EXAMPLE 27

7 g of a mixture of 6-ethyl-3-methyl-octen-(5)-ol-(1) and the corresponding octene-(6)-isomer in 50 ml of methanol are hydrogenated at 20° under atmosphere pressure in the presence of 1 g of Raney-nickel. The hydrogenation is taken to conclusion in the autoclave at 60° and 20 atm. After removal of the catalyst, the product is distilled. There are thus obtained 6.6 g of 6-ethyl-3-methyl-octanol-(1). B.p. 92°/3 mm; $n_D^{20} = 1.4435$; yield 93.3%.

G: Manufacture of compounds of formula XII:

EXAMPLE 28

A solution of 10 g of trans 3,6-dimethyl-octen-(2)-yne-(4)-diol-(1,6) in 200 ml of dry toluene is shaken for 1 hour at 25° in the presence of 200 g of dry manganese dioxide. The manganese dioxide is then filtered off and well washed with toluene. After evaporation of the solvent, there are obtained 8.1 g of crude product and therefrom, by distillation, pure trans 6-hydroxy-3,6-dimethyl-octen-(2)-yn-(4)-al. B.p. 105°–108°/0.15 mm; $n_D^{20} = 1.5280$. Yield 82.2%.

H: Manufacture of compounds of formula XIII:

EXAMPLE 29

40 g of the product obtained according to Example 28 are dissolved in 200 ml of ethyl acetate and hydrogenated under atmospheric pressure at 20° in the presence of 5 g of 5% palladium/carbon. After the uptake of approximately 2/3 of the theoretical amount of hydrogen, the rate of hydrogenation slows down. A further 5 g of catalyst are therefore added and the hydrogenation taken to conclusion. After filtration of the catalyst, there are obtained 41.7 g of crude product which is purified by means of metabisulphite. After working up, there are obtained 24.4 g of crude 6-hydroxy-6-ethyl-3-methyl-octanal [yield 60% based on 3,6-dimethyl-octen-(2)-yne-(4)-diol-(1,6)]. B.p. 88°/0.03 mm; $n_D^{20} = 1.4580$; $d_4^{20} = 0.9493$.

I: Manufacture of compounds of formula XIV:

EXAMPLE 30

100 g of d,1-3,6-dimethyl-octanol-(1) in 100 ml of water are added, while stirring, to a mixture (cooled to 7°) of 330 g sodium bichromate and 330 g of concentrated sulfuric acid in 2200 ml of water. After extraction and usual working up, there are obtained 70.1 g of crude d,1-3,6-dimethyl-octanal-(1), which are distilled. B.p. 62°/4mm; $d_4^{20} = 0.8328$; $n_D^{20} = 1.4288$. Odour: floral, green, very strong.

K: Manufacture of compounds of formula XV:

EXAMPLE 31

15.1 g of a mixture of d,1-6-ethyl-3-methyl-octen-(5)-al-(1) and of the corresponding octene-(6)-isomer are kept for 3 days at room temmperature with 150 ml of absolute ethanol and 2 g of p-toluenesulfonic acid. After the addition of 20 g of dry sodium carbonate, the mixture is filtered and the ethanol distilled off in vacuo. The residue is taken up in ether and the solution washed with water. After drying and evaporating off the solvent, there are obtained 19.0 g of crude product, the distillation of which gives 15.2 g of the diethyl acetal of cis, trans-6-ethyl-3-methyl-octen-(6)-al-(1). B.p. 109°/5mm; $d_4^{20} = 0.8587$; $n_D^{20} = 1.4405$. Floral odour of roses and lilac.

L: Manufacture of compounds of formula XVI:

EXAMPLE 32

By esterification of d,1-3,6-dimethyl-octanol-(1) by means of acetic anhydride to which 2 per cent by weight thereof of o-phosphoric acid has been added, there is obtained the corresponding acetate, d,1-1-acetoxy-3,6-dimethyl-octane, of b.p. 88°/4 mm; $d_4^{20} = 0.8772$; $n_D^{20} = 1.4285$. Yield 87%. Odour: rose-like, aldehydic.

EXAMPLE 33

By esterification of d,1-6-ethyl-3-methyl-octanol-(1) by means of acetic anhydride to which 5 per cent by weight thereof of o-phosphoric acid, has been added, there is obtained the corresponding acetate, d,1-1-acetoxy-6-ethyl-3-methyloctane, of b.p. 100°/4 mm; $d_4^{20} = 0.8758$; $n_D^{20} = 1.4335$. Odour slightly floral, reminiscent of lily of the valley.

EXAMPLE 34

10 g of formic acid (98%) are added slowly, at 45°, to 20 g of acetic anhydride. After 2 hours, there are added, while stirring, at 5°–10°, 21.6 g of d,1-6-ethyl-3-methyl-octanol-(1) and the mixture is left for 3 days at 20°. After working up there are obtained 20.3 g of the corresponding formate, d,1-1-formoxy-6-ethyl-3-methyl-octane, of b.p. 93°/4 mm; $d_4^{20} = 0.8814$; $n_D^{20} = 1.4340$. Yield 81%. Odour of bran.

EXAMPLE 35

By esterification, in a manner analogous to that described in Example 34, of d,1-3,6-dimethyl-octanol-(1), there is obtained the corresponding formate, d,1-1-formoxy-3,6-dimethyloctane, of b.p. 77°/4 mm; $d_4^{20} = 0.8778$; $n_D^{20} = 1.4285$. Yield 88%. Odour: green, rose-like.

The foregoing illustrates the practice of this invention which, however, is not to be limited thereby but is to be construed as broadly as permissible in view of the prior art and limited solely by the appended claims.

We claim:

1. A racemic compound having the formula

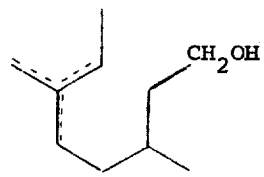

wherein
the dotted lines indicate that one double bond emanates from the 6-position, or mixtures of two or more of said compounds.

2. A racemic compound having the formula

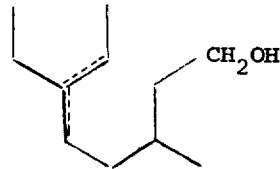

wherein
the dotted lines indicate that one double bond emanates from the 6-position, or mixtures of two or more of said compounds.

3. A mixture of compounds having the structural formula set forth in claim 1.

4. A mixture of compounds having the structural formula set forth in claim 2.

5. A mixture as set forth in claim 3 wherein said mixture comprises 3,6-dimethyl-octen-(5)-ol-(1); 3,6-dimethyl-octen-(6)-ol-(1) and 6-ethyl-3-methyl-hepten-(6)-ol-(1).

6. A mixture as set forth in claim 4, wherein said mixture comprises 6-ethyl-3-methyl-octen-(5)-ol-(1) and 6-ethyl-3-methyl-octen-(6)-ol-(1).

* * * * *